US009869545B2

(12) United States Patent
Burnside et al.

(10) Patent No.: US 9,869,545 B2
(45) Date of Patent: Jan. 16, 2018

(54) DATA ACQUISITION DEVICES, SYSTEMS AND METHOD FOR ANALYZING STRAIN SENSORS AND MONITORING TURBINE COMPONENT STRAIN

(71) Applicant: General Electric Company, Schenectady, NY (US)

(72) Inventors: Jason Lee Burnside, Greenville, SC (US); Gregory Lee Hovis, Martinez, GA (US); William F. Ranson, Columbia, SC (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 15/384,513

(22) Filed: Dec. 20, 2016

(65) Prior Publication Data

US 2017/0102229 A1 Apr. 13, 2017

Related U.S. Application Data

(63) Continuation of application No. 14/687,170, filed on Apr. 15, 2015, now Pat. No. 9,557,164.

(51) Int. Cl.
| | |
|---|---|
| *G01B 11/16* | (2006.01) |
| *G01B 11/24* | (2006.01) |
| *G01M 5/00* | (2006.01) |
| *G06T 7/90* | (2017.01) |
| *G01N 21/27* | (2006.01) |
| *G02B 23/24* | (2006.01) |

(52) U.S. Cl.
CPC .............. *G01B 11/16* (2013.01); *G01B 11/24* (2013.01); *G01M 5/0091* (2013.01); *G01N 21/27* (2013.01); *G06T 7/90* (2017.01); *G02B 23/2484* (2013.01)

(58) Field of Classification Search
CPC G01B 11/16; G01B 11/25; G01L 1/24; G06T 7/408
See application file for complete search history.

(56) References Cited

U.S. PATENT DOCUMENTS

| | | |
|---|---|---|
| 4,528,856 A | 7/1985 | Junker et al. |
| 4,746,858 A | 5/1988 | Metala et al. |
| 4,782,705 A | 11/1988 | Hoffmann et al. |

(Continued)

FOREIGN PATENT DOCUMENTS

WO WO 2014/031957 2/2014

*Primary Examiner* — Kara E Geisel
*Assistant Examiner* — Maurice Smith
(74) *Attorney, Agent, or Firm* — Dority & Manning, P.A.

(57) ABSTRACT

Data acquisition devices for analyzing reference objects and systems for monitoring turbine component deformation are provided. A data acquisition device has a longitudinal axis and includes a lens assembly and an image capture device in communication with the lens assembly for receiving and processing light from the lens assembly to generate images. The data acquisition device further includes a light source and a light tube coupled at a rear end to the light source. The light tube extends along the longitudinal axis between a front end and the rear end, and is operable to transport light from the light source therethrough and emit the light from the front end. The data acquisition device further includes an actuator operable to activate the image capture device and the light source.

11 Claims, 8 Drawing Sheets

(56) References Cited

U.S. PATENT DOCUMENTS

| | | | |
|---|---|---|---|
| 4,859,062 A | 8/1989 | Thurn et al. | |
| 6,078,396 A | 6/2000 | Manzouri | |
| 6,175,644 B1 | 1/2001 | Scola et al. | |
| 6,574,363 B1 * | 6/2003 | Classen | H04N 9/643 348/E9.04 |
| 6,796,939 B1 * | 9/2004 | Hirata | A61B 1/00036 600/109 |
| 6,983,659 B2 | 1/2006 | Soechting et al. | |
| 6,986,287 B1 | 1/2006 | Dorfman | |
| 7,200,259 B1 | 4/2007 | Gold et al. | |
| 7,227,648 B2 | 6/2007 | Weinhold | |
| 7,414,732 B2 | 8/2008 | Maidhof et al. | |
| 7,421,370 B2 | 9/2008 | Jain et al. | |
| 7,441,464 B2 | 10/2008 | Turnbull et al. | |
| 7,477,995 B2 | 1/2009 | Hovis et al. | |
| 7,490,522 B2 | 2/2009 | Ruehrig et al. | |
| 7,533,818 B2 | 5/2009 | Hovis et al. | |
| 7,689,003 B2 | 3/2010 | Shannon et al. | |
| 7,697,966 B2 | 4/2010 | Monfre et al. | |
| 7,849,752 B2 | 12/2010 | Gregory et al. | |
| 8,245,578 B2 | 8/2012 | Ranson et al. | |
| 8,307,715 B2 | 11/2012 | Ranson | |
| 8,511,182 B2 | 8/2013 | Bjerge et al. | |
| 8,514,278 B2 * | 8/2013 | Karpen | A61B 1/00036 348/69 |
| 8,600,147 B2 | 12/2013 | Iliopoulos et al. | |
| 8,818,078 B2 | 8/2014 | Telfer et al. | |
| 8,994,845 B2 | 3/2015 | Mankowski | |
| 9,128,063 B2 | 9/2015 | Dooley | |
| 9,200,889 B2 | 12/2015 | Swiergiel et al. | |
| 9,207,154 B2 | 12/2015 | Harding et al. | |
| 9,311,566 B2 | 4/2016 | Iliopoulos et al. | |
| 9,316,571 B2 | 4/2016 | Müller et al. | |
| 2005/0010081 A1 * | 1/2005 | Doguchi | A61B 1/00009 600/109 |
| 2010/0310128 A1 * | 12/2010 | Iliopoulos | G01B 11/165 382/103 |
| 2013/0013224 A1 | 6/2013 | Ito et al. | |
| 2013/0194567 A1 | 8/2013 | Wan et al. | |
| 2013/0286236 A1 * | 10/2013 | Mankowski | H04N 5/23222 348/222.1 |
| 2014/0000380 A1 | 1/2014 | Slowik et al. | |
| 2014/0267677 A1 | 9/2014 | Ward, Jr. et al. | |
| 2015/0239043 A1 | 8/2015 | Shipper, Jr. et al. | |
| 2016/0161242 A1 | 6/2016 | Cook et al. | |
| 2016/0313114 A1 | 10/2016 | Tohme et al. | |
| 2016/0354174 A1 | 12/2016 | Demir | |

* cited by examiner

DATA ACQUISITION DEVICES, SYSTEMS AND METHOD FOR ANALYZING STRAIN SENSORS AND MONITORING TURBINE COMPONENT STRAIN

RELATED APPLICATIONS

This application is a continuation application of U.S. Non-Provisional Patent Application Ser. No. 14/687,170 having a filing date of Apr. 15, 2015, the disclosure of which is incorporated by reference herein in its entirety.

FIELD OF THE INVENTION

The present disclosure relates generally to data acquisition devices and methods for analyzing reference objects such as strain sensors, and to systems for monitoring turbine component strain which utilize such devices to analyze strain sensors.

BACKGROUND OF THE INVENTION

Turbomachines are widely utilized in fields such as power generation and aircraft engines. For example, a conventional gas turbine system includes a compressor section, a combustor section, and at least one turbine section. The compressor section is configured to compress air as the air flows through the compressor section. The air is then flowed from the compressor section to the combustor section, where it is mixed with fuel and combusted, generating a hot gas flow. The hot gas flow is provided to the turbine section, which utilizes the hot gas flow by extracting energy from it to power the compressor, an electrical generator, and other various loads.

During operation of a turbomachine, various components (collectively known as turbine components) within the turbomachine and particularly within the turbine section of the turbomachine, such as turbine blades, may be subject to creep due to high temperatures and stresses. For turbine blades, creep may cause portions of or the entire blade to elongate so that the blade tips contact a stationary structure, for example a turbine casing, and potentially cause unwanted vibrations and/or reduced performance during operation.

Accordingly, it is desirable to monitor turbine components for creep. One approach to monitoring turbine components for creep is to configure strain sensors on the components, and analyze the strain sensors at various intervals to monitor for deformations associated with creep strain. However, such deformation can in many cases be on the order of 0.01% of an original dimension, thus requiring specialized equipment for strain monitoring. Presently known acquisition tools and techniques for monitoring such strain sensors may in some cases not provide the desired sufficiently low-distortion, high-contrast, small scale images for these applications.

Accordingly, alternative systems and methods for monitoring turbine component strain are desired in the art. Further, alternative data acquisition devices and methods for analyzing reference objects, such as strain sensors, are desired in the art. Systems, devices and methods which provide sufficiently low-distortion, high-contrast, small scale images for turbine component strain sensor monitoring would be particularly advantageous.

BRIEF DESCRIPTION OF THE INVENTION

Aspects and advantages of the invention will be set forth in part in the following description, or may be obvious from the description, or may be learned through practice of the invention.

In accordance with one embodiment of the present disclosure, a data acquisition device for analyzing a reference object is provided. The data acquisition device has a longitudinal axis and includes a lens assembly and an image capture device in communication with the lens assembly for receiving and processing light from the lens assembly to generate images. The data acquisition device further includes a light source and a light tube coupled at a rear end to the light source. The light tube extends along the longitudinal axis between a front end and the rear end, and is operable to transport light from the light source therethrough and emit the light from the front end. The data acquisition device further includes an actuator operable to activate the image capture device and the light source.

In accordance with another embodiment of the present disclosure, a system for monitoring turbine component deformation is provided. The turbine component has an exterior surface. The system includes a strain sensor configurable on the exterior surface of the turbine component, and a data acquisition device for analyzing the strain sensor. The data acquisition device includes a lens assembly and an image capture device in communication with the lens assembly for receiving and processing light from the lens assembly to generate images. The data acquisition device further includes a light source, and a light tube coupled at a rear end to the light source. The light tube extends along a longitudinal axis between a front end and the rear end, and is operable to transport light from the light source therethrough and emit the light from the front end. The data acquisition device further includes an actuator operable to activate the image capture device and the light source, and a shell, the shell surrounding the lens assembly, the image capture device, the light source, and the light tube. The data acquisition device further includes a plurality of spacers disposed proximate the front end of the light tube. Each of the plurality of spacers extends from the shell and is sized to space the front end of the light tube from the exterior surface of the turbine component when the data acquisition device is in an operative position in contact with the exterior surface of the turbine component.

In accordance with another embodiment of the present disclosure, a method for analyzing a strain sensor is provided. The method includes locating a strain sensor portion relative to a background portion within an image of the strain sensor by performing a first analysis of the image. The method further includes identifying strain sensor indicia of the strain sensor portion by performing a second analysis of the image. The method further includes conducting a quality analysis of the strain sensor portion by performing a third analysis of the strain sensor portion of the image, the third analysis utilizing a higher bit-depth than the first analysis.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Figure 1:
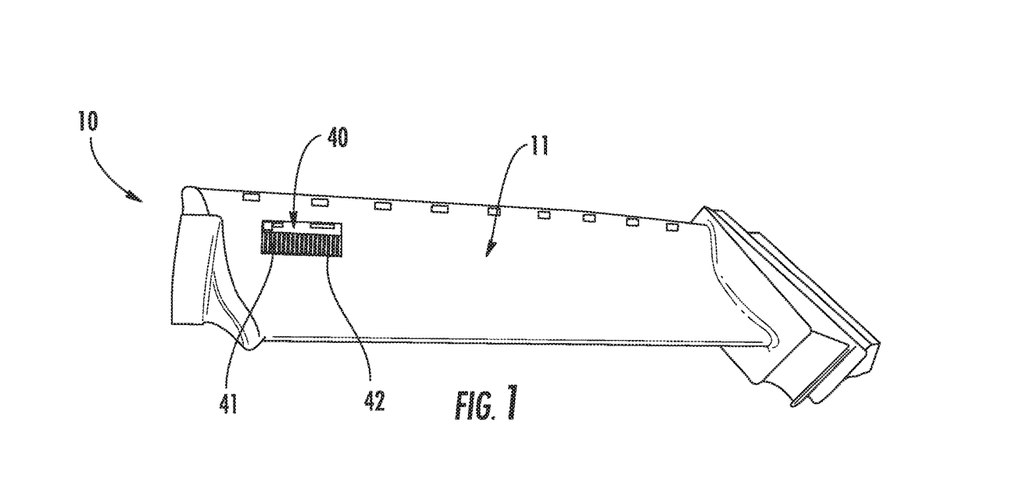
FIG. 1 is a perspective view of an exemplary turbine component comprising a strain sensor in accordance with one embodiment of the present disclosure.

Referring now to FIG. 1, a turbine component 10 is illustrated with a strain sensor 40 configured on a portion of the turbine component's exterior surface 11. The turbine component 10 can comprise a variety of specific components such as those utilized in high temperature applications (e.g., components comprising nickel or cobalt based superalloys). For example, in some embodiments, the turbine component 10 may comprise a combustion component or hot gas path component. In some particular embodiments, the turbine component 10 may comprise a bucket, blade, vane, nozzle, shroud, rotor, transition piece or casing. In other embodiments, the turbine component 10 may comprise any other component of a turbine such as a component for a gas turbine, industrial gas turbine, steam turbine or the like.

The turbine component 10 has an exterior surface 11 on which strain sensors 40 are configured. Strain sensors 40 in accordance with the present disclosure may be configured on the exterior surface 11 using any suitable techniques, including deposition techniques; other suitable additive manufacturing techniques; subtractive techniques such as laser ablation, engraving, machining, etc.; appearance-change techniques such as annealing, direct surface discoloration, or techniques to cause local changes in reflectivity; mounting of previously formed strain sensors 40 using suitable mounting apparatus or techniques such as adhering, welding, brazing, etc.; or identifying pre-existing characteristics of the exterior surface 11 that can function as the components of a strain sensor 40.

Figure 2:
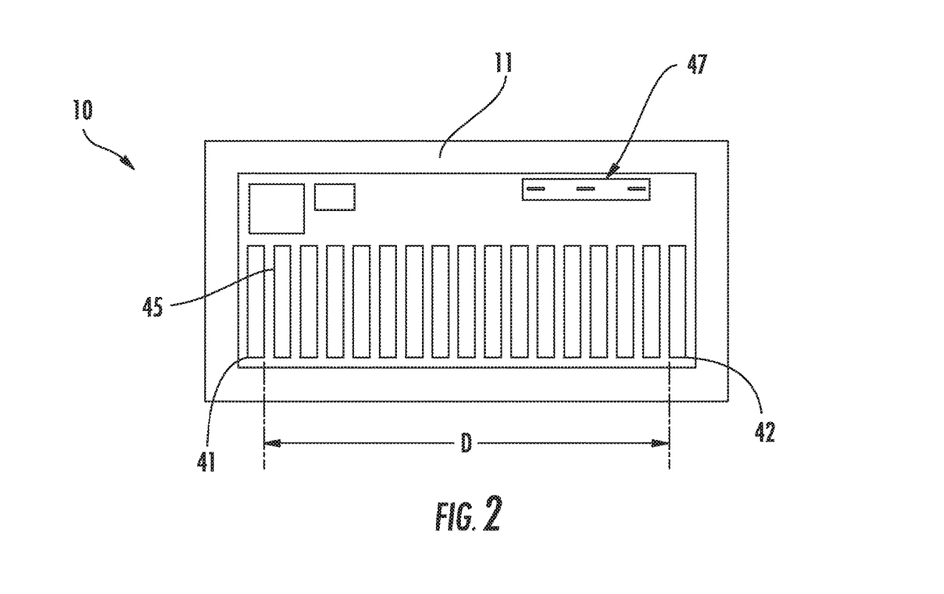
FIG. 2 is a top view of an exemplary strain sensor in accordance with one embodiment of the present disclosure.

Referring now to FIGS. 1 and 2, a strain sensor 40 is configured on a portion of the exterior surface 11 of the turbine component 10. The strain sensor 40 generally comprises at least two reference points 41 and 42 that can be used to measure a distance D between said at least two reference points 41 and 42 at a plurality of time intervals. As should be appreciated to those skilled in the art, these measurements can help determine the amount of strain, strain rate, creep, fatigue, stress, etc. at that region of the turbine component 10. The at least two reference points 41 and 42 can be disposed at a variety of distances and in a variety of locations depending on the specific turbine component 10 so long as the distance D there between can be measured. Moreover, the at least two reference points 41 and 42 may comprise dots, lines, circles, boxes or any other geometrical or non-geometrical shape so long as they are consistently identifiable and may be used to measure the distance D there between.

The strain sensor 40 may comprise a variety of different configurations and cross-sections such as by incorporating a variety of differently shaped, sized, and positioned reference points 41 and 42. For example, as illustrated in FIG. 2, the strain sensor 40 may comprise a variety of different reference points comprising various shapes and sizes. Such embodiments may provide for a greater variety of distance measurements D such as between the outer most reference points (as illustrated), between two internal or external reference points, or any combination there between. The greater variety may further provide a more robust strain analysis on a particular portion of the turbine component 10 by providing strain measurements across a greater variety of locations.

Furthermore, the dimensions of the strain sensor 40 may depend on, for example, the turbine component 10, the location of the strain sensor 40, the targeted precision of the measurement, application technique, and optical measurement technique. For example, in some embodiments, the strain sensor 40 may comprise a length and width ranging from less than 1 millimeter to greater than 300 millimeters. Moreover, the strain sensor 40 may comprise any thickness that is suitable for application and subsequent optical identification without significantly impacting the performance of the underlying turbine component 10. Notably, this thickness may be a positive thickness away from the surface 11 (such as when additive techniques are utilized) or a negative thickness into the surface 11 (such as when subtractive techniques are utilized). For example, in some embodiments, the strain sensor 40 may comprise a thickness of less than from about 0.01 millimeters to greater than 1 millimeter. In some embodiments, the strain sensor 40 may have a substantially uniform thickness. Such embodiments may help facilitate more accurate measurements for subsequent strain calculations between the first and second reference points 41 and 42.

In some embodiments, the strain sensor 40 may comprise a positively applied square or rectangle wherein the first and second reference points 41 and 42 comprise two opposing sides of said square or rectangle. In other embodiments, the strain sensor 40 may comprise at least two applied reference points 41 and 42 separated by a negative space 45 (i.e., an area in which the strain sensor material is not applied). The negative space 45 may comprise, for example, an exposed portion of the exterior surface 11 of the turbine component 10. Alternatively or additionally, the negative space 45 may comprise a subsequently applied visually contrasting material that is distinct from the material of the at least two reference points 41 and 42 (or vice versa).

As illustrated in FIG. 2, in some embodiments, the strain sensor 40 may include a unique identifier 47 (hereinafter "UID"). The UID 47 may comprise any type of barcode, label, tag, serial number, pattern or other identifying system that facilitates the identification of that particular strain sensor 40. In some embodiments, the UID 47 may additionally or alternatively comprise information about the turbine component 10 or the overall turbine that the strain sensor 40 is deposited on. The UID 47 may thereby assist in the identification and tracking of particular strain sensors 40, turbine components 10 or even overall turbines to help correlate measurements for past, present and future operational tracking.

The strain sensor 40 may thereby be configured in one or more of a variety of locations of various turbine components 10. For example, as discussed above, the strain sensor 40 may be configured on a bucket, blade, vane, nozzle, shroud, rotor, transition piece or casing. In such embodiments, the strain sensor 40 may be configured in one or more locations known to experience various forces during unit operation such as on or proximate airfoils, platforms, tips or any other suitable location. Moreover, the strain sensor 40 may be deposited in one or more locations known to experience elevated temperatures. For example the strain sensor 40 may be configured on a hot gas path or combustion turbine component 10.

In some embodiments, multiple strain sensors 40 may be configured on a single turbine component 10 or on multiple turbine components 10. For example, a plurality of strain sensors 40 may be configured on a single turbine component 10 (e.g., a bucket) at various locations such that the strain may be determined at a greater number of locations about the individual turbine component 10. Alternatively or additionally, a plurality of like turbine components 10 (e.g., a plurality of buckets) may each have a strain sensor 40 configured in a standard location so that the amount of strain experienced by each specific turbine component 10 may be compared to other like turbine components 10. In even some embodiments, multiple different turbine components 10 of the same turbine unit (e.g., buckets and vanes for the same turbine) may each have a strain sensor 40 configured thereon so that the amount of strain experienced at different locations within the overall turbine may be determined.

Figure 3:
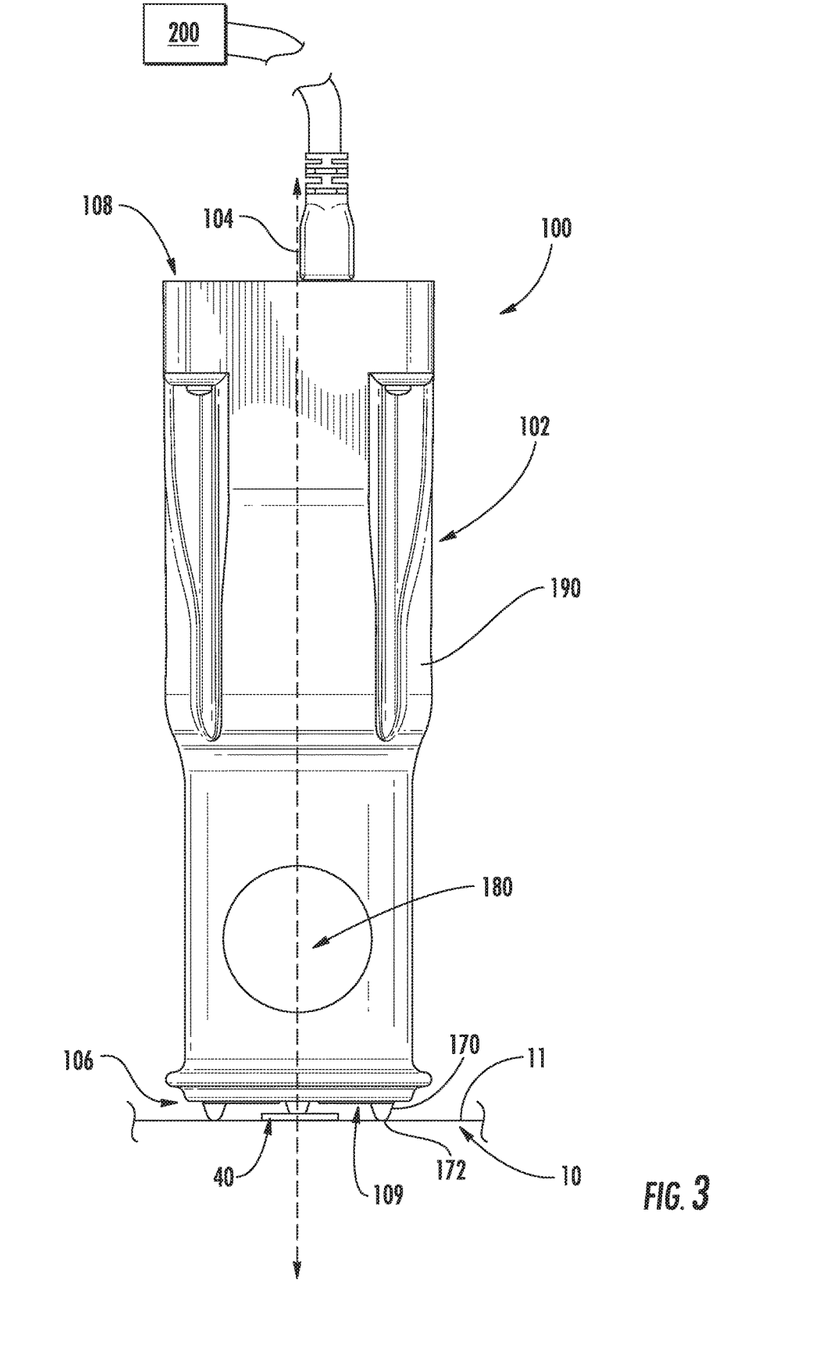
FIG. 3 is a side view of a system for monitoring turbine component strain in accordance with one embodiment of the present disclosure.

Referring now to FIG. 3, a system 100 for monitoring turbine component 10 deformation is provided. System 100 may include, for example, one or more strain sensors 40 which are configurable on the exterior surface 11 of one or more turbine components 10 as discussed above. Further, system 100 may further include a data acquisition device 102 for analyzing one or more reference objects, such as strain sensors 40.

Data acquisition devices 102 in accordance with the present disclosure may advantageously facilitate improved strain sensor 40 analysis. In particular, such data acquisition devices 102 may advantageously provide low-distortion, high-contrast, small scale images which are particularly useful for turbine component 10 strain sensor 40 monitoring. For example, in some embodiments, data acquisition devices 102 in accordance with the present disclosure can provide images having up to approximately 15 micron resolution, up to 0.001 millimeter overall accuracy, and/or measurement accuracy up to 5 microstrain or 0.000005 inch/inch. To provide such images, and as discussed herein, data acquisition devices 102 in accordance with the present disclosure advantageously include a number of image optimization features, such as for example features for providing optimal light source standoff distances and light angles as well as features for providing optimal, consistent imaging angles relative to the reference object(s) being imaged, such as strain sensors 40.

Referring now to FIGS. 3 through 7, embodiments of data acquisition devices 102 in accordance with the present disclosure are provided. A device 102 in accordance with the present disclosure defines and extends along a longitudinal axis 104 between a front end 106 and a rear end 108. The front end 106 may generally be the end that contacts a surface, such as an external surface 11 of a turbine component 10, for imaging purposes. As discussed herein, device 102 may be positioned such that the front end 106 is in contact with a surface such as an external surface 11, and further positioned such that a reference object such as a strain sensor 40 is within a viewing window 109 of the device 102. The viewing window 109 can generally be defined as the area visible to a lens assembly 110 of the device 102. Light may then be received and processed by an image capture device 120 to generate images, and these images may be analyzed as discussed herein.

Device 102 may thus include, for example, a lens assembly 110 and an image capture device 120. Lens assembly 110 may generally extend between a front end 112 and a rear end 114 along the longitudinal axis 104, and may magnify images viewed by the lens assembly 110 for processing by the image capture device 120. Lens assembly 110 in some embodiments may, for example, be a suitable camera lens, telescope lens, etc., and may include one or more lens spaced apart to provide the required magnification. Notably, the required magnification for applications as discussed herein is not necessarily significantly large, and may for example, be approximately 0.5 to approximately 2 times magnification or more.

Figure 5:
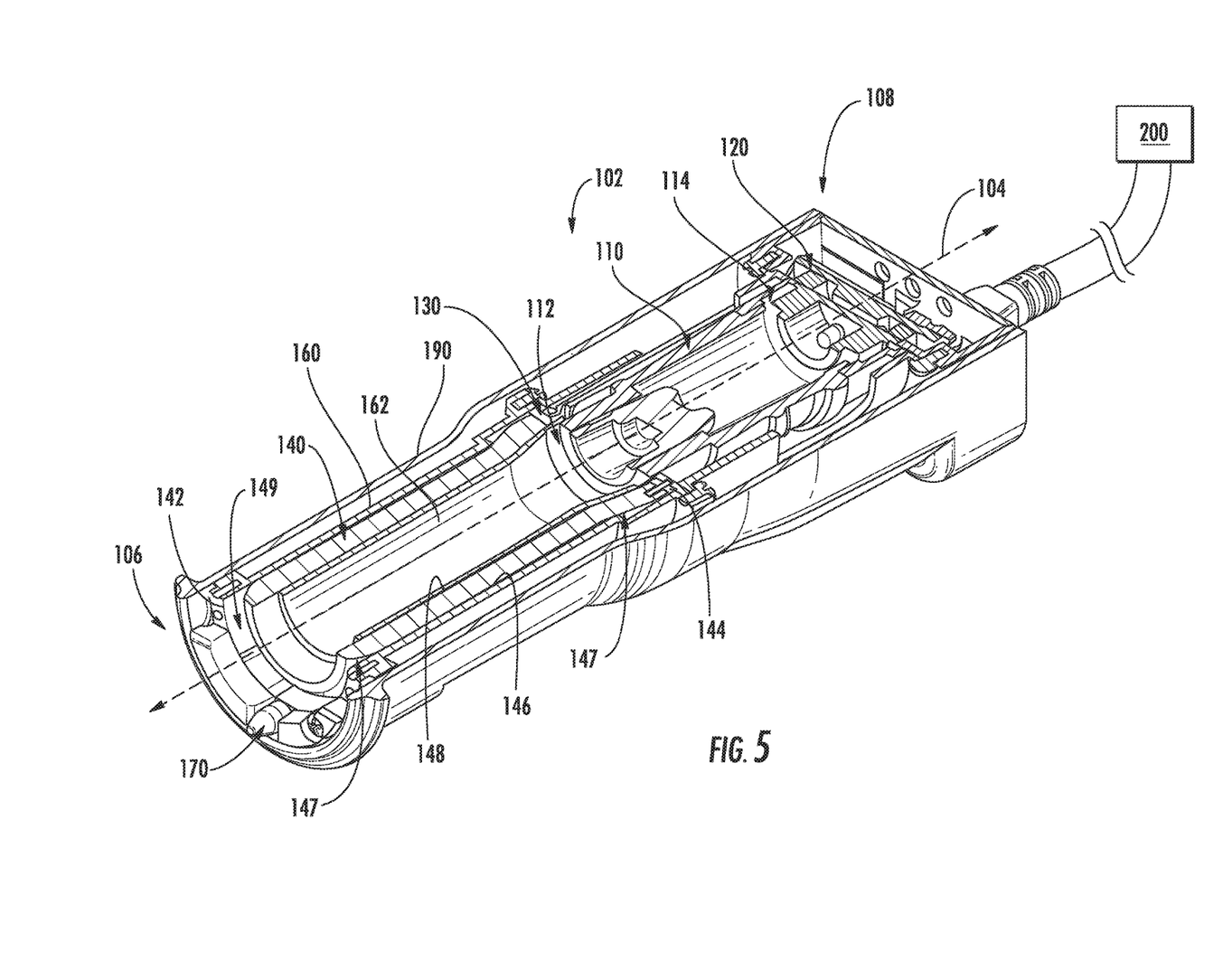
FIG. 5 is a perspective cross-sectional view of a data acquisition device in accordance with one embodiment of the present disclosure.
Figure 6:
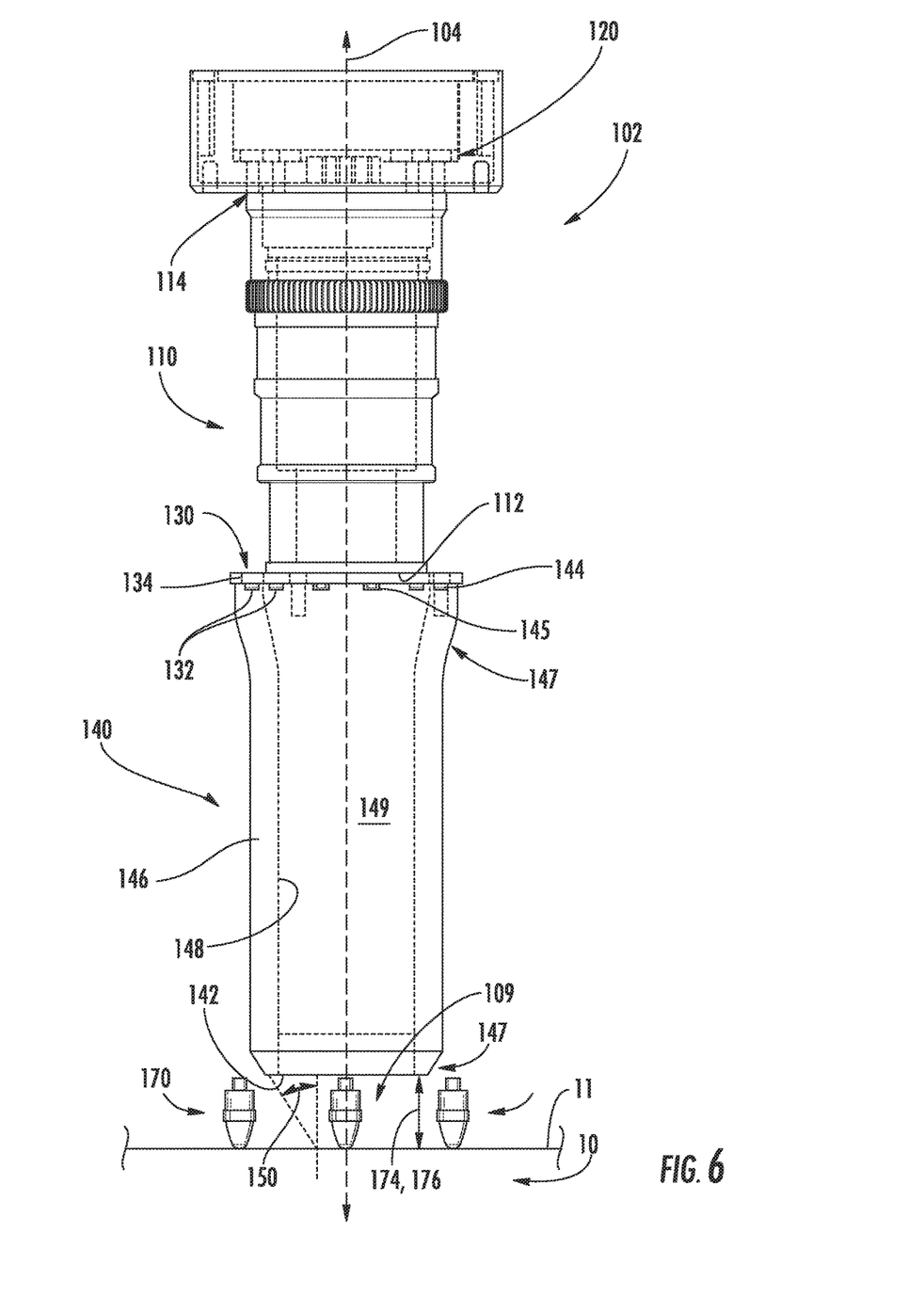
FIG. 6 is a side view of a data acquisition device, with various components shown in shadow for illustrative purposes, in accordance with one embodiment of the present disclosure.

Image capture device 120 may generally be in communication with the lens assembly 110 for receiving and processing light from the lens assembly 110 to generate images. In exemplary embodiments, for example, image capture device 120 may be a camera sensor which receives and processes light from a camera lens to generate images, such as digital images, as is generally understood. Notably, the required resolution for applications as discussed herein is not necessarily significantly large, and may for example, be approximately 1.5 Megapixels or more.

Image capture device 120 may further be in communication with suitable hardware and/or software, via for example a suitable wired or wireless connection, for storing and analyzing the images from the image capture device 120 and device 102 generally. Such hardware and/or software may, for example, generally analyze strain sensors 40 to determine whether deformation and strain have occurred as discussed above.

Device 102 can further, for example, include a light source 130. Light source may generally provide light to illuminate a reference object, such as a strain sensor 40, for imaging purposes. Light source 130 is, in exemplary embodiments as shown, spaced from the front end 106 of the device 102. For example, light source 130 may be positioned proximate the front end 112 of the lens assembly 110, which may be spaced from the front end 106 of the device 102. Light source 130 may include, for example, one or more light emitting diodes ("LEDs") or other light emitting components 132. The light emitting components 132 may, for example, be spaced apart in an annular array. Light source 130 may further include a ring 134 on which the light emitting components 132 are mounted and positioned. The light source 130 and light emitting components 132 thereof may generally be selectively activatable and, when activated, may provide light which provides illumination within the viewing window 109.

Figure 7:
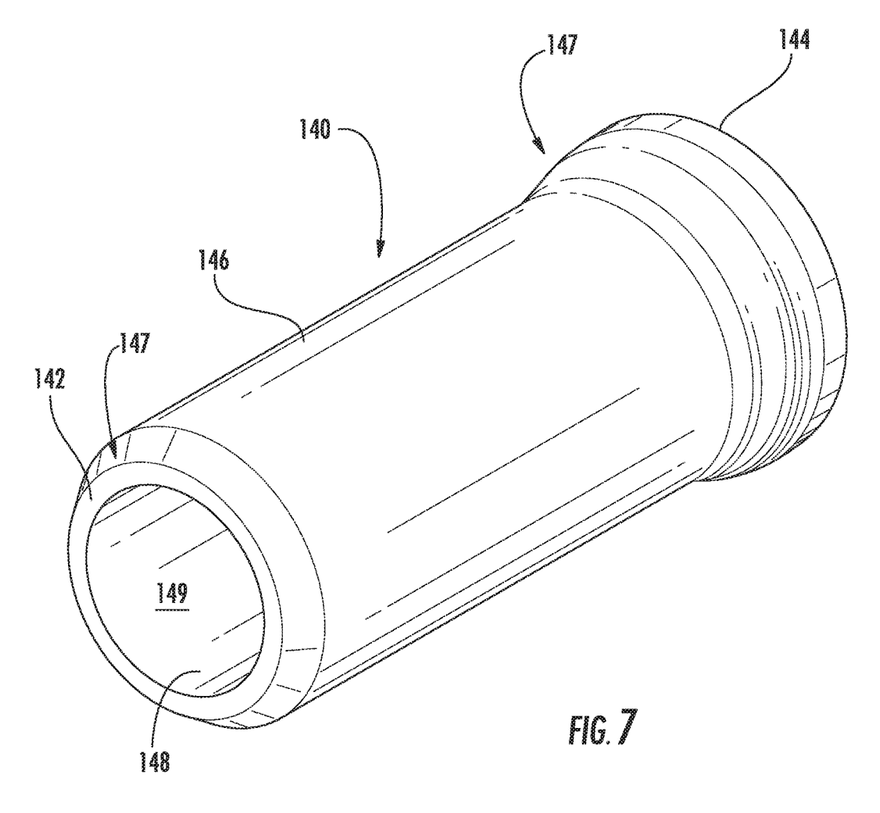
FIG. 7 is a perspective view of a light tube of a data acquisition device in accordance with one embodiment of the present disclosure.

Device 102 can further, for example, include a light tube 140 which is operable to transmit light from the light source 130 therethrough. Light tube 140 extends along the longitudinal axis 104 between a front end 142 and a rear end 144, and is operable to transport light therethrough and emit the light from the front end 142. For example, in exemplary embodiments as shown, light tube 140 may be coupled at its rear end 144 to the light source 130, such that the light tube 140 and light source 130 are in contact. The light emitting components 132, for example, may be positioned within recesses 145 defined in the rear end 144 of the light tube 140. When light is emitted from the light source 130, such as from the light emitting components 132 thereof, this light may travel through the light tube 140 and be emitted from the front end 142.

Light tube 140 may, for example, be formed from a suitable plastic which allows light travel therethrough. For example, in exemplary embodiments, light tube 140 may be formed from a translucent plastic, which may or may not be transparent. In some embodiments, light tube 140 may be formed from a material that has a critical exposure of between approximately 10 mJ/cm$^2$ and approximately 14 mJ/cm$^2$ and/or an exposure that gives 0.010 inch thickness of between approximately 50 mJ/cm$^2$ and approximately 60 mJ/cm$^2$.

As mentioned, light travels through the light tube 140 from the rear end 144 towards the front end 142, and is emitted from the front end 142. In some exemplary embodiments, an outer surface 146 of the light tube 140 may include one or more chamfered portions 147, which can assist in focusing and aiming the light as it travels through the light tube 140 for optimal output. Each chamfered portion 147 of the outer surface 146 may taper towards an inner surface 148 (which defines an interior 149 of the light tube 140) along the longitudinal axis 104. For example, as shown, a chamfered portion 147 may be provided proximate the rear end 144 to initially focus the light after it enters the light tube 140. Additionally or alternatively, a chamfered portion 147 may be provided at the front of the light tube 140. This chamfered portion 147 may be proximate or may include the front end 142. In particular when this chamfered portion 147 includes the front end 142, this chamfered portion 147 may focus the light as it is emitted from the front end 142 for optimal light distribution within the viewing window 109. For example, in exemplary embodiments as shown, light may be emitted from the front end 142 at an angle of incidence 150 of between approximately 20 degrees and approximately 50 degrees, such as between approximately 30 degrees and approximately 45 degrees. An angle of incidence within this range may provide optimal light distribution within the viewing window 109, particularly when viewing reference features on turbine components, and in exemplary embodiments may be due to the chamfered portion 147 that includes the front end 142.

In exemplary embodiments as illustrated, light tube 140 is generally cylindrical, thus having a circular cross-sectional shape. Alternatively, however, light tube 140 may have an oval, rectangular, triangular, or any other suitable polygonal cross-sectional shape.

Notably, light tube 140 also defines the viewing window 109. Specifically, the inner surface 148 and interior 149 define the viewing window 109. Images of a reference object, when the device 102 is in position on the surface on which the reference object is configured, are visible to the lens assembly 110 and received by the image capture device 120 through the interior 149, as illustrated. Accordingly, front end 112 of lens assembly 110 may be positioned proximate rear end 144 of light tube 140.

To prevent loss of light due to emission from the light tube 140 before the light reaches the front end 142, an outer shroud 160 and/or and inner shroud 162 may in exemplary embodiments be included in the data acquisition device 102. The shrouds 160, 162 may be positioned proximate and optionally in contact with the outer and inner surface 146, 148 of the light tube 140, respectively, and be formed form opaque materials which prevent light from travelling therethrough. Accordingly, light that encounters the shrouds 160, 162 as it is travelling through the light tube 140 may be redirected within the light tube 140, rather than being allowed to escape. For example, in exemplary embodiments one or both shrouds 160, 162 may be formed from a suitable metal, such as aluminum. Outer shroud 160 may surround at least a portion of the outer surface 146 of the light tube 140, and inner shroud 162 may surround at least a portion of the inner surface 148 of the light tube 140.

Figure 4:
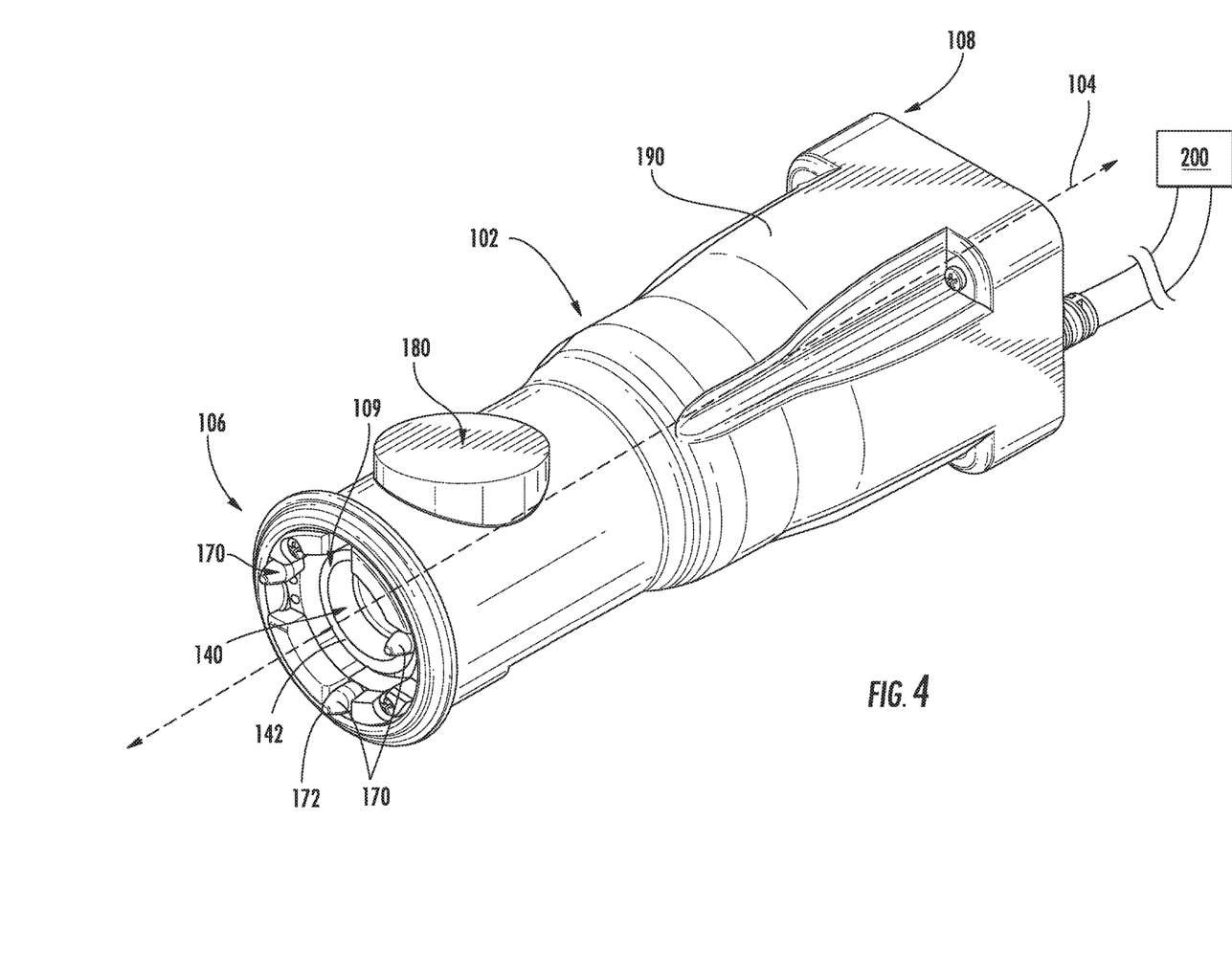
FIG. 4 is a perspective view of a data acquisition device in accordance with one embodiment of the present disclosure.

To further facilitate optimal lighting of the positioning of the viewing window 109, device 102 may further include one or more spacers 170 which are disposed proximate the front end 142 of the light tube 140. In exemplary embodiments, three spacers 170 are utilized, such that the device 102 can be optimally balanced on surfaces, such as exterior surfaces 11, that are both planer and surfaces that are non-planer. However, it should be understood that any suitable number of spacers is within the scope and spirit of the present disclosure.

The spacers 170 are sized and positioned to provide optimal spacing between the light tube 140 and the exterior surface 11 when the device 102 is in an operative position in contact with a surface on which a reference object is configured, such that optimal lighting of the reference objected is provided and optimal images are received by the image capture device 120 from the lens assembly 110. For example, in exemplary embodiments, each spacer may be sized such that a distance 174 along the longitudinal axis 104 between a front end 172 of each of the plurality of spacers 170 and the front end 142 of the light tube 140 is between approximately 0.25 inches and approximately 0.75 inches, such as between approximately 0.4 inches and approximately 0.5 inches. Thus, each spacer 170 may be sized to space the front end 142 of the light tube 140 from the exterior surface 11 of the turbine component 10 or other object by a distance 176 along the longitudinal axis 104 of between approximately 0.25 inches and approximately 0.75 inches, such as between approximately 0.4 inches and approximately 0.5 inches, when the device 102 is in an operative position in contact with the exterior surface 11 of the turbine component 10 or other object.

Device 102 may, in exemplary embodiments, further include an actuator 180. Actuator 180 may, for example, be a button, switch, or other suitable component which can be operated to activate other components of the device 102. For example, actuator 180 may be in communication (via a suitable wired or wireless connection) with the image capture device 120 and the light source 130. When the actuator 180 is actuated to activate the image capture device 120 and the light source 130, the light emitting components 132 may be activated to emit light and the image capture device 120 may be activated to receive one or more images. These components may then be deactivated, either automatically or manually due to additional actuation of the actuator 180.

Device 102 may additionally include a shell 190 which generally surrounds and contains various other components of the device 102. For example, shell 190 may surround the lens assembly 110, the image capture device 120, the light source 130, and the light tube 140. Shell 190 may further surround the actuator 180, which may be actuatable through the shell 190, or the actuator 180 may protrude through the shell 190. Notably, the front ends 172 of the spacers 170 may extend outwardly from the shell 190 along the longitudinal axis 104, to space the shell 190 from a surface when the device 102 is in an operative position as discussed.

It should be noted that, in exemplary embodiments, devices 102 as discussed herein are hand-held devices which may be manually operated for image analysis as discussed herein. However, it should be understood that the present disclosure is not limited to hand-held devices. Rather, any suitable devices, including for example automated devices and/or devices attached to, for example, robotic machines, etc., and which are manually operated or automated, are within the scope and spirit of the present disclosure.

Figure 8:
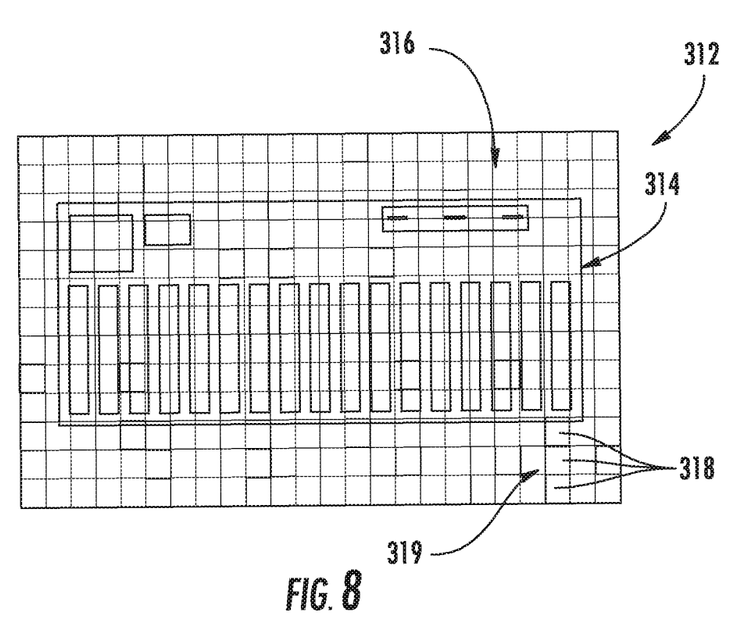
FIG. 8 illustrates an image of a strain sensor in accordance with one embodiment of the present disclosure.
Figure 9:
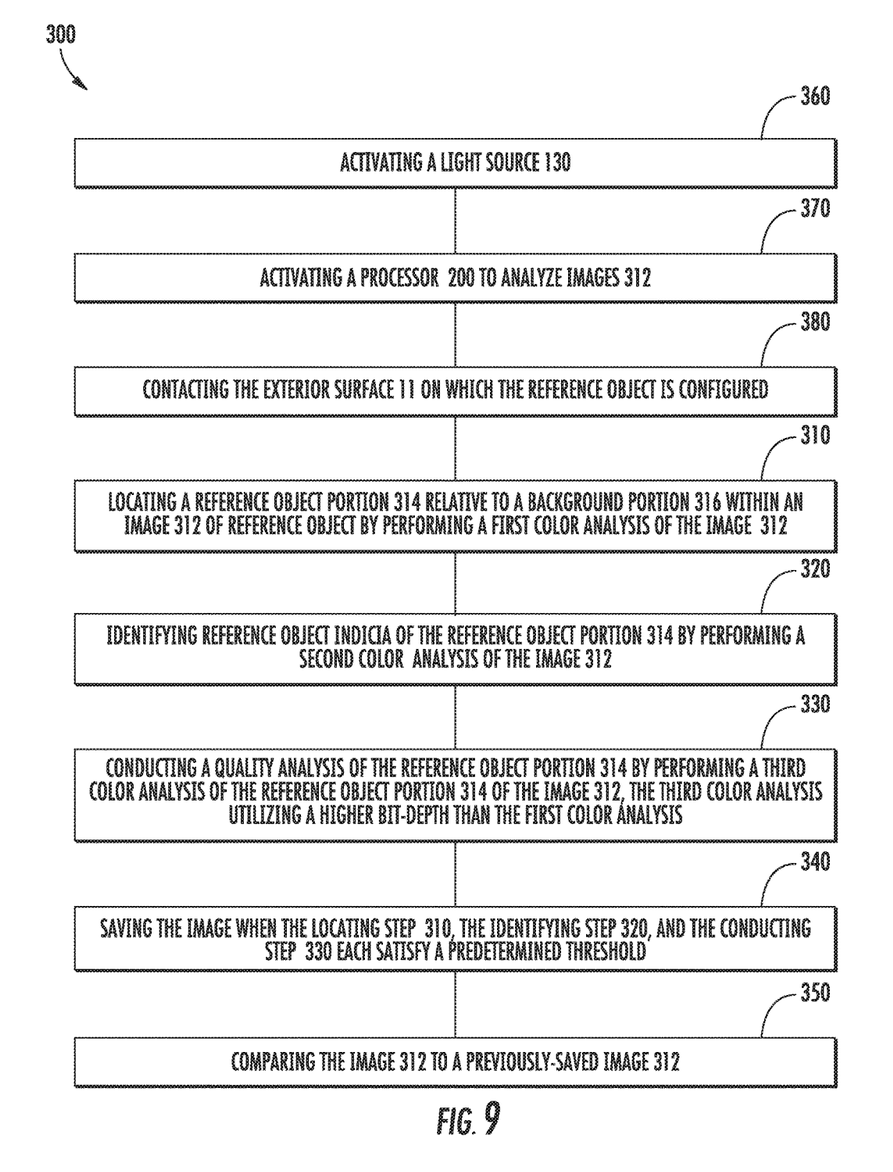
FIG. 9 is a flow chart illustrating a method in accordance with one embodiment of the present disclosure.

Referring now to FIGS. 8 and 9, the present disclosure is further directed to methods 300 for analyzing reference objects, such as strain sensors 40. In exemplary embodiments, an image capture device 120 may be utilized to obtain images that are analyzed via a method 300 in accordance with the present disclosure. However, it should be understood that the present disclosure is not limited image capture devices 120 and images captured therefrom, and rather that any suitable images of references objects may be analyzed in accordance with the present disclosure.

As mentioned, an image capture device 120 may be in communication with suitable hardware and/or software, via for example a suitable wired or wireless connection, for storing and analyzing the images from the image capture device 120 and device 102 generally. Accordingly, an image capture device 120 may further include a processor 200 which may include such suitable hardware and/or software. In exemplary embodiments, processor 200 may perform various of the steps of method 300 as discussed herein.

In general, as used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Processor 200 may also include various input/output channels for receiving inputs from and sending control signals to various other components with which the processor 200 is in communication, such as the lens assembly 110, light source 130, image capture device 200, etc.

Method 300 may include, for example, the step 310 of locating a reference object portion 314 (such as a strain sensor portion 314) relative to a background portion 316 within an image 312 of the reference object (such as the strain sensor 40) by performing a first analysis of the image 312. The first analysis is generally an analysis which differentiates the reference object portion 314 from the background portion 316 on the basis of differences in color depth. First analysis may be performed on each individual pixel 318 or groups of pixels 319 defining the image 312. For example, in exemplary embodiments, a binary color depth analysis is performed on multi-pixel groups 319. For a binary analysis to occur, the number of bits-per-pixel of the image i.e. 128, 256, etc., is divided into two groups (generally a group which includes the lighter color depths and a group which includes the darker color depths). Each group is categorized as a reference object portion 314 or a background portion 316. For example, the binary color depth analysis may categorize pixels or multi-pixel groups 319 that are darker color depths as denoting a reference object portion 314, and may categorize pixels or multi-pixel groups 319 that are lighter color depths as denoting a background portion 316.

In alternative embodiments, first analysis need not be a binary analysis. For example, first analysis may be a suitable greyscale analysis, as discussed herein, or other suitable comparison of color depths of the pixels 318 defining the image 312.

Step 310 may generally locate the reference object portion 314 within the image 312. Further, in some embodiments, the information obtained from the first analysis may then be compared to predetermined threshold(s) for such information to determine if the threshold is satisfied. A predetermined threshold may, for example, include one or more dimensions of the reference object, desired locations and orientation of the reference object portion 314 in the plane of the image 312, etc. In some embodiments, if the predetermined threshold is satisfied, feedback signals may be provided to the device 102 to indicate such satisfaction. For example, indicator lights 195 may be activated.

Method 300 may further include, for example, the step 320 of identifying reference object indicia (such as strain sensor indicia) of the reference object portion 314 by performing a second analysis of the image 312 (such as the entire image 312 or the reference object portion 314 thereof). For strain sensors 40, strain sensor indicia may include, for example, reference points 41, 42, unique identifiers 47, and other identifiable components of the strain sensors 40. In general, reference object indicia are identifiable components of the reference object which provide some information about the reference object.

The second analysis is generally an analysis which further differentiates the reference object portion 314 from the background portion 316, and which differentiates the various reference object indicia, on the basis of differences in color depth. Second analysis may be performed on each individual pixel 318 or groups of pixels 319 defining the image 312. For example, in exemplary embodiments, a binary color depth analysis is performed on single pixels 318. In alternative embodiments, second analysis need not be a binary analysis. For example, second analysis may be a suitable greyscale analysis, as discussed herein, or other suitable comparison of color depths of the pixels 318 defining the image 312.

Step 320 may generally further locate the reference object portion 314 within the image 312, and may further facilitate collection of information from the reference object of which the image 312 was taken. For example, the existence of reference points 41, 42 may be confirmed, and identifying information for the reference object may be collected from the unique identifiers 47. Further, in some embodiments, the information obtained from the second analysis may then be compared to predetermined threshold(s) for such information to determine if the threshold is satisfied. A predetermined threshold may, for example, include predetermined levels of indicia, such as reference points 41, 42, which can be confirmed.

Method 300 may further include, for example, the step 330 of conducting a quality analysis of the reference object portion 314 by performing a third analysis of the image 312

(such as the entire image 312 or the reference object portion 314 thereof). The third analysis is generally an analysis which further differentiates the reference object portion 314 from the background portion 316, and which further differentiates the various reference object indicia, on the basis of differences in color depth. In exemplary embodiments, third analysis utilizes a higher bit-depth than the first analysis. Further, in some embodiments, third analysis may utilize a higher bit-depth than the second analysis. Third analysis may be performed on each individual pixel 318, or on sub-sections of individual pixels. For example, pixels 318 may be divided into 100 sub-sections, 1000 sub-sections, 10,000 sub-sections, or any other suitable number of sub-sections, and the third analysis may be performed on each individual sub-section. In exemplary embodiments, a greyscale analysis is performed on the bits-per-pixel of the image i.e. 128, 256, etc. For example, in some embodiments, a 256 bit-per-pixel greyscale analysis is performed. Accordingly, each pixel 318 or sub-section thereof is categorized as having a particular color depth per the 128, 256, etc. color depth scale.

Step 330 may generally allow for the strength of the image 312 to be analyzed by, for example, analyzing the contrast between neighboring pixels 318 or sub-sections thereof. For example, it is generally desirable for the contrast between pixels at the border of features of the reference object portion 314, such as the edges of the reference object portion 314 or indicia thereof, to be high, thus indicating the distinction between the reference object portion 314 or indicia thereof and the background portion 316, etc. Further, step 330 may generally allow for the sharpness of the image 312 to be analyzed by, for example, analyzing the width in pixels 318 or sub-sections thereof of various features of the reference object portion 314. For example, it is generally desirable for the width of features of the reference object portion 314, such as the edges of the reference object portion 314 or indicia thereof, to be low, thus indicating the sharpness of the image of the reference object portion 314 or indicia thereof relative to the background portion 316, etc. Further, in some embodiment, the information obtained from the third analysis may then be compared to predetermined threshold(s) for such information to determine if the threshold is satisfied. A predetermined threshold may, for example, include predetermined strength and sharpness levels.

Steps 310, 320 and/or 330 may generally be utilized to determine whether an image 312 is of sufficient quality to be saved for subsequent analysis, such as subsequent strain analysis as discussed herein. For example, as discussed, in some embodiments, the information obtained from the color analyses in each step 310, 320, 330 may compared to various predetermined thresholds. In exemplary embodiments, method 300 may further include the step 340 of saving the image 312 when the locating step 310, the identifying step 320 and/or the conducting step 330 each satisfy the required predetermined threshold(s). Such image 312 may then be utilized in subsequent analysis of the reference object.

In some embodiments, method 300 may further include the step 350 of comparing the saved image 312 to one or more previously-saved images 312. The previously-saved images 312 are generally images 312 that have been saved within the same iteration of reference object analysis, i.e. during the same operation of the device 102 and processor 200 to obtain images during a particular time period. In general, differences between the reference object portions 314, such as differences between the indicia thereof, may be analyzed. Optimally, little or no differences should be present, because the images are taken during a single iteration. In general, a threshold may be set for particular differences, such as a threshold strain. For example, a threshold strain may be 5 microstrain, 10 microstrain, 20 microstrain, etc. If a difference exceeds the threshold, this may indicate that outside forces are influencing the accuracy of the images, thus allowing a user to cease analysis and perform a quality check of the associated system 100, device 102, processor 200, etc.

It should be noted that steps 310, 320 and/or 330 as discussed herein may in exemplary embodiments, be performed in real time as images are received by the processor 200 from image captures device 120.

Method 300 may further include various steps for initially operating a device, such as device 102, to analyze a reference object. For example, method 300 may include the step 360 of activating a light source, such as light source 130. Light source 130 may be activated (such as by processor 200) either automatically within an automated system or manually in response to an input by a user, such by a user pressing actuator 180. Further, method 300 may include the step 370 of activating the processor 200 to analyze images. In accordance with this step, the processor 200 may enter a mode wherein steps 310, 320 and/or 330 are performed. Such activation may occur (such as by processor 200) either automatically within an automated system or manually in response to an input by a user, such by a user pressing actuator 180. Further, method 300 may include the step 380 of contacting the exterior surface on which the reference object is configured, such as the exterior surface 11 of the turbine component 10, with a device such as device 102. In exemplary embodiments as discussed herein, spacers 170 may contact the exterior surface 11. Such contact may occur either automatically within an automated system (such as by processor 200) or manually by a user. Notably, in exemplary embodiments, step 370 may occur after step 360. Steps 310-350 may occur after such steps.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for analyzing a strain sensor, the method comprising:
    providing a data acquisition device, the data acquisition device comprising an image capture device for receiving and processing light to generate images of the strain sensor, the image capture device comprising a processor;
    activating a light source of the data acquisition device for analyzing the strain sensor;
    emitting light from the light source through a light tube;
    focusing and aiming the light with one or more chamfered portions of the light tube as the light travels through the light tube;
    locating, with the processor, a strain sensor portion relative to a background portion within an image of the strain sensor by performing a first analysis of the image;

identifying, with the processor, strain sensor indicia of the strain sensor portion by performing a second analysis of the image; and conducting, with the processor, a quality analysis of the strain sensor portion by performing a third analysis of the strain sensor portion of the image, the third analysis utilizing a higher bit-depth than the first analysis.

2. The method of claim 1, wherein the first analysis is a binary analysis of multi-pixel groups of the strain sensor portion of the image.

3. The method of claim 1, wherein the second analysis is a binary analysis of single pixels of the strain sensor portion of the image.

4. The method of claim 1, wherein the third analysis is a 256 bit-per-pixel greyscale analysis.

5. The method of claim 1, further comprising the step of saving the image when the locating step, the identifying step, and the conducting step each satisfy a predetermined threshold.

6. The method of claim 5, further comprising comparing the image to a previously-saved image.

7. The method of claim 1, further comprising comparing a result of the first analysis to a predetermined threshold for the first analysis to determine if the predetermined threshold is satisfied.

8. The method of claim 1, further comprising comparing a result of the second analysis to a predetermined threshold for the second analysis to determine if the predetermined threshold is satisfied.

9. The method of claim 1, further comprising comparing a result of the third analysis to a predetermined threshold for the third analysis to determine if the predetermined threshold is satisfied.

10. The method of claim 1, wherein the light tube extends between a front end and a rear end, and emitting light from the light source through the light tube comprises transporting the light through the light tube and emitting the light from the front end of the light tube.

11. The method of claim 1, wherein emitting light from the light source through the light tube comprises emitting light from the light source into a rear end of the light tube coupled to the light source, transporting the light through a translucent material of the light tube, and emitting the light from a front end of the light tube.

* * * * *